United States Patent [19]

Lal et al.

[11] Patent Number: 5,416,094
[45] Date of Patent: May 16, 1995

[54] ANTIARRHYTHMIC AND CARDIOPROTECTIVE SUBSTITUTED -1(2H)ISOQUINOLINES, MEDICAMENT CONTAINING THEM, AND THEIR USE FOR COMBATING HEART FAILURES

[75] Inventors: Bansi Lal; Ramesh Gidwani; Ramanujam Rajagopalan; Radha Panicker; Chinnakulandai Sankar, all of Bombay, India; Hans-Jochen Lang; Heinrich Englert, both of Hofheim/Taunus, Germany; Wolfgang Scholz, Eschborn, Germany

[73] Assignee: Hoechst Aktiengesellschaft, Frankfurt am Main, Germany

[21] Appl. No.: 126,200

[22] Filed: Sep. 24, 1993

[30] Foreign Application Priority Data

Sep. 28, 1992 [EP] European Pat. Off. ........... 92116535

[51] Int. Cl.⁶ .................... C07D 217/12; A61K 31/47
[52] U.S. Cl. .................... 514/307; 546/140; 546/141; 546/143; 546/144; 546/146; 544/128; 544/333; 544/363; 514/233.5; 514/255; 514/256; 514/308; 514/309; 514/310
[58] Field of Search ............... 546/146, 140, 141, 143, 546/144, 146; 544/128, 333, 363; 514/233.5, 255, 256, 307, 308, 309, 310

[56] References Cited

U.S. PATENT DOCUMENTS 3,780,027 12/1973 Cragoe et al. ............... 549/494
4,260,611 4/1981 Bartmann et al. ............ 546/146
4,322,418 3/1982 Lösel et al. ................. 546/146
4,673,682 6/1987 Konz et al. ................. 514/307

FOREIGN PATENT DOCUMENTS 0005231 11/1979 European Pat. Off. ........ 546/146
0105210 4/1984 European Pat. Off. ........ 546/146
4154768 5/1992 Japan ........................ 546/146

OTHER PUBLICATIONS

European Search Report dated Jan. 11, 1994 for corresponding EP Application No. 93 11 5081.

*Primary Examiner*—C. Warren Ivy
*Assistant Examiner*—Zinna N. Davis
*Attorney, Agent, or Firm*—Finnegan, Henderson, Farabow, Garrett & Dunner

[57] ABSTRACT

Described are guanidinocarbonyl isoquinolines of the formula I,

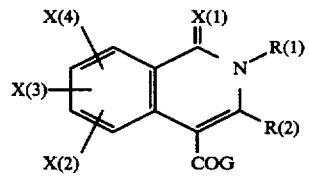

wherein R(1) is hydrogen, (amino) (cyclo) (aryl)alk(e-n)yl (heteroaryl); R(2) is hydrogen, halogen, alkyl, or aryl; G is a radical of the formula VII:

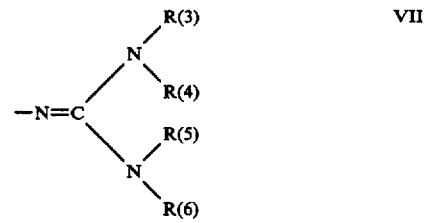

X(2), X(3) and X(4) are hydrogen, halogen, nitro, amino, alkyl, sulfonamide, (mono) (di) (lower alkyl) (amino), benzyloxy, hydroxy; X(1) hydrogen, oxygen, sulfur and NR(7)R(8), and their pharmaceutically acceptable salts; described is also a process for their preparation, their use as medicaments, and medicaments containing them for treating congestive heart failure, and arrhythmic conditions as well as cardioprotective agents in mammals.

7 Claims, No Drawings

ANTIARRHYTHMIC AND CARDIOPROTECTIVE SUBSTITUTED -1(2H)ISOQUINOLINES, MEDICAMENT CONTAINING THEM, AND THEIR USE FOR COMBATING HEART FAILURES

The invention relates to isoquinolines of the formula I:

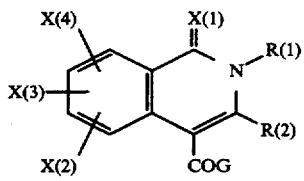

wherein

R(1) is hydrogen, alkyl, cycloalkyl, arylalkyl, alkenyl, substituted amino alkyl or an aryl or heteroaryl ring, which rings are unsubstituted or substituted with one to three groups including halogen, nitro, amino, mono(lower alkyl)amino, di(lower alkyl)amino, lower alkyl, lower alkoxy, benzyloxy, phenoxy, hydroxy, or trifluoromethyl, R(2) is hydrogen, halogen, alkyl, or aryl which may be unsubstituted or may have one to three groups including halogen, nitro, amino, mono(lower alkyl)amino, di(lower alkyl)amino, lower alkyl, lower alkoxy, benzyloxy, phenoxy, a hydroxy, G is a radical of the formula VII

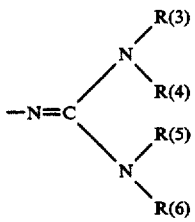

X(2), X(3) and X(4) individually or collectively are selected from hydrogen, halogen, nitro, amino, alkyl, sulfonamide, mono(lower alkyl)amino, di(lower alkyl)amino, lower alkyl, benzyloxy, hydroxy and a combination thereof, X(1) is two hydrogen atoms, oxygen, sulfur or NR(7), in which R(7) is hydrogen, alkyl, cycloalkyl, arylalkyl, alkenyl, substituted amino alkyl or an aryl or heteroaryl ring, which rings are unsubstituted or substituted with one to three groups including halogen, nitro, amino, mono(lower alkyl)amino, di(lower alkyl)amino, lower alkyl, lower alkoxy, benzyloxy, phenoxy, hydroxy, or trifluoromethyl, in which substituents any alkyl chain or alkenyl chain may be interrupted by oxygen, sulfur or NR(8), wherein R(8) is hydrogen, alkyl, cycloalkyl, arylalkyl, alkenyl, substituted amino alkyl or an aryl or heteroaryl ring, which rings are unsubstituted or substituted with one to three groups including halogen, nitro, amino, mono(lower alkyl)amino, di(lower alkyl)amino, lower alkyl, lower alkoxy, benzyloxy, phenoxy, hydroxy, or trifluoromethyl, and their pharmaceutically acceptable salts.

Preferred are compounds I in which

R(1) is aryl or heteroaryl with no substitution or substituted with one to three groups including halogen, nitro, amino, mono(lower alkyl)amino, di(lower alkyl)amino, lower alkyl, lower alkoxy, benzyloxy, phenoxy, hydroxy, or trifluoromethyl, R(2) is hydrogen, or alkyl, G is a radical of the formula VII:

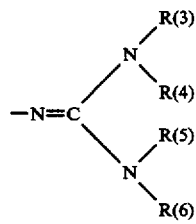

with R(3), R(4), R(5) and R(6) being hydrogen,

X(2), X(3) and X(4) individually or collectively are selected from hydrogen, halogen, nitro, amino, alkyl, sulfonamide, mono(lower alkyl)amino, di(lower alkyl)amino, lower alkyl, benzyloxy, hydroxy and a combination thereof, X(1) is oxygen.

Particularly preferred are compounds I wherein:

R(1) is lower alkyl, lower alkyloxy, or a phenyl, naphthyl, or pyridyl ring the rings being unsubstituted or substituted with one to three groups including halogen, nitro, amino, mono(lower alkyl)amino, di(lower alkyl)amino, lower alkyl, lower alkoxy, benzyloxy, phenoxy, hydroxy, or trifluoromethyl, R(2) is hydrogen, G is a radical of the formula VII:

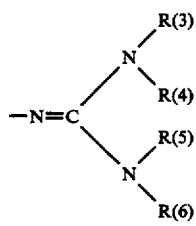

with R(3), R(4), R(5) and R(6) being hydrogen,

X(2), X(3) and X(4) individually or collectively are hydrogen, halogen, nitro, amino, alkyl, sulfonamide, mono(lower alkyl)amino, di(lower alkyl)amino, lower alkyl, benzyloxy, hydroxy and a combination thereof, and X(1) is oxygen.

Most preferred are compounds wherein

R(1) is lower alkyl, lower alkyloxy, or phenyl, naphthyl or pyridyl rings the rings being unsubstituted or substituted with Cl, R(2) is hydrogen, G is a radical of the formula VII:

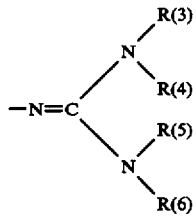

with R(3), R(4), R(5) and R(6) being hydrogen,

X(2), X(3) and X(4) individually or collectively are hydrogen, halogen, nitro, amino, alkyl, sulfonamide, mono(lower alkyl)amino, di(lower alkyl)amino, lower alkyl, benzyloxy, hydroxy and a combination thereof, and X(1) is oxygen.

As used throughout the specification and the claims, the term "alkyl" refers to a straight or branched chain hydrocarbon radical containing no unsaturation and having 1 to 6 carbon atoms such as methyl, ethyl, 1-propyl, 2-propyl, 1-butyl, 1-pentyl, 2-pentyl, 3-hexyl and the like. Further it is possible to interrupt the chain by O, S or NR(8). The term "alkenyl" refers to straight or branched chain hydrocarbons with at least one unsaturation and having 3–6 carbon atoms such as allyl, isopropenyl, isobutenyl and the like; this chain may be interrupted by oxygen, sulfur or NR(8). The term "lower" as applied to any of the aforementioned groups refers to a group having a carbon skeleton containing up to and including 6-carbon atoms. The term "cycloalkyl" refers to a substituted or unsubstituted saturated or unsaturated cyclic carbon skeleton of 3–8 carbon atoms, such as cyclopropyl, cyclobutyl, cyclopentyl, cyclohexyl, cyclohexenyl, cycloheptyl and like. The term "halogen" refers to F, Cl, Br or I. The term "aryl" includes substituted and unsubstituted phenyl and heteroaromatics. The notation "heterocycles", includes hetero aromatics such as pyridyl, thienyl, furyl, indolyl, quinolyl, isoquinolyl, pyrimidyl, triazolyl, benzothiazolyl and the like, saturated heterocycles such as pyrrolidines, piperidines, morpholines and piperazines. Guanidino refers to unsubstituted—$N=C(NH_2)_2$ and its tautomeric forms and substituted guanidino refers to a radical of the formula VII:

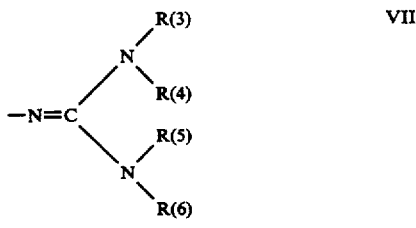

wherein R(3), R(4), R(5), R(6) may be individually or collectively hydrogen, lower alkyl, acyl, aryl, or cycloalkyls. Alkyl and cycloalkyls are as defined earlier; acyl may be a branched or straight chain acyl group of $C_1-C_6$ units. NR(3)R(4) or NR(5)R(6) may be the part of a heterocyclic structure such as piperidine, pyrrolidine, morpholine or piperazines and the like. The term "arylalkyl" is a group which has a substituted phenyl connected through an alkyl group, for substituted phenyl is defined ealier, similarly alkyl may be a chain of carbon $C_1-C_6$ both straight or branched. Above substituted guanidine may also exists in a tautomeric form. R(7) and R(8) carry the same meaning as for R(1). All isomers, tautomers, and stereoisomers are included.

Compounds of the formula I carry a substituted acylguanidine in its skeleton. Amiloride a pyrazine with an acylguanidine may be as a representative, it is a potassium sparing diuretic. Several derivatives of amiloride are reported, dimethylamiloride or ethylisopropylamiloride are well known derivatives in this series

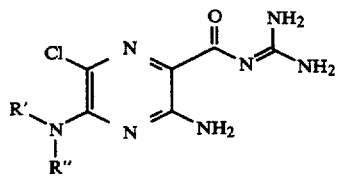

Amiloride: R' and R" = H
Dimethylamiloride: R' and R" = $CH_3$
Ethylisopropylamiloride R' = Et; R" = i-Pr.

Amiloride has antiarrhythmic properties [Circulation 79, 1257 (1989)]. Its weak antiarrhythmic properties associated with hypotensive and saluretic action restricts its wide use, as these side effects are detrimental in the treatment of cardiac arrhythmias. The amiloride derivative ethylisopropylamiloride [(Eur. Heart J.9 (Suppl.1): 167 (1988)](book of abstracts) was found to suppress completely an artificially induced ventricular fibrillation.

In U.S Pat. No. 3 780 027 acylguanidines are claimed. They have no structural resemblance to the inventive compounds. These compounds have strong saluretic action as they are derived from commercially available diuretics such as bumetanide and furosemide, further these compounds carry an amino group, which is important for saluretic action.

It was very surprising that the compounds according to the invention show very good antiarrhythmic properties without saluretic properties. Due to this pharmacological effect, the compounds are ideally suitable as antiarrhythmic pharmaceuticals having a cardioprotective component for infarct prophylaxis and infarct treatment and also for the treatment of angina pectoris. The invention also relates to the process for the preparation of compounds of formula I. The synthesis of compounds of formula I was carried out by using an intermediate of formula II,

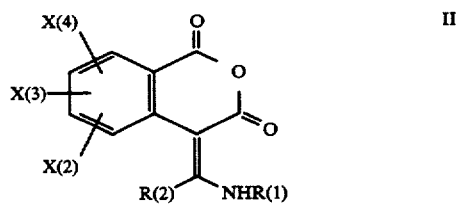

which in turn is made through a reported method (Otto. S. Wolbeis, Liebigs. Ann. Chem, 1981, 819–827). 5-Methylhomophthalic acid used for the preparation of compounds of formula II was made from 2,4-dimethylbenzoic acid by a similar method reported in the literature (G. B. Henderson and R. A. Hill, J. C. S., Perkin Trans. I, p. 1111, 1982). Compounds of formula II are converted into isoquinolinones of formula III,

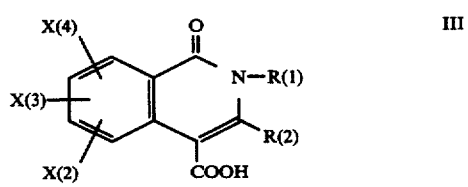

on treatment with 10% NaOH or on treatment with an acid (C. D. Patil, G. S. Sadana and K. D. Deodhar; J.

Ind. chem Soc; 67, 654–656, 1990 and the references therein). Compounds of the formula III may also be prepared directly by condensation of the formula VI

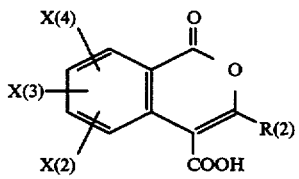

(M. Kimura; I. Waki; Y. Deguchi; K. Amemiya and T. Maeda. Chem. Pharm. Bull. Jap. 31, 1277, 1983) with primary amine $NH_2R(1)$. Values of R(1), R(2), X(2), X(3) and X(4) for formula II, III, IV and VI have the same meaning as defined above for formula I. The majority of the compounds reported here are unknown.

The invention also relates to a process for the preparation of compounds of formula I, which comprises:
reacting compounds of formula IV

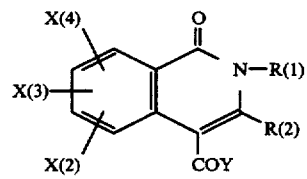

with either free guanidine or with a compound of formula V

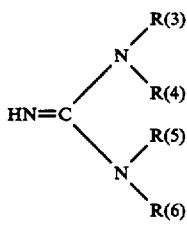

in which R(3), R(4), R(5) and R(6) have values as defined earlier and Y is a leaving group, which can be easily displaced by a nucleophile.

The activated acid derivatives of the formula IV in which Y is an alkoxy group, preferably a methoxy group, an activated phenoxy group, a phenylthio, methylthio, 2-pyridylthio group or a nitrogen heterocycle, such as imidazolyl, which can be prepared from acid chloride (formula IV; Y=Cl) which in turn can be prepared from acid, formula III on treatment with thionyl chloride. Other activating ester methods can be used, which are known in the peptide area to activate the acid for coupling reaction. The imidazolides of formula IV, Y=imidazolides, can also be prepared from a compound of formula III by treating it with 1,1-Carbonyldiimidazole [C.Staab, Angew. Chem. Int. (Ed. Eng. 1 351-367 (1962)]. Compound of formula IV (Y=Cl) on treatment with the the compound of formula V under Schotten-Baumann condition, also gave compound of formula I. Other mixed anhydrides related to formula IV may be prepared, such as with ClCOOEt, tosyl chloride, triethylphosphoryl chloride in the presence of triethylamine or any other base in an inert solvent. Activation of the COOH group in the compounds of the formula III can also be achieved with DCC(dicyclohexylcarbodiimid). Other methods of preparation of activated carboxylic acid derivative of formula IV type are given with indication of source literature in J. March, Advanced Organic Chemistry, 3rd Edition (John Wiley & Son, 1985), p. 350. Coupling reaction between compounds of formula III and V can be conducted in a variety of ways in protic or aprotic polar solvents, but inert organic solvents are preferred. In this connection methanol, THF, DMF, N-methylpyrrolidone, hexamethyl phosphoric acid triamide (HMPA). etc., at from room temperature up to the boiling point of these solvents have proved suitable for the reaction of the Formula IV (Y=OMe) with guanidine. Reactions of compound IV with salt free guanidine are advantageously carried out in aprotic inert solvents such as THF, dimethoxy ethane, DMF or dioxane. However water can also be used as a solvent. In the case where a compound of formula III is directly treated with Carbonyldiimidazole for activating the carboxy group, aprotic polar solvents such as DMF, or dimethoxy ethane are used, followed by the addition of a compound of formula V.

Compounds of the formula I may be converted into pharmacologically acceptable acid addition salts.

Acids useful for preparing the pharmaceutically acceptable acid addition salts of the invention include inorganic acid such as hydrochloric, hydrobromic, sulfuric, nitric, phosphoric and perchloric acids, as well as organic acids such as tartaric, citric, acetic, succinic, maleic, fumaric, methanesulfonic and oxalic acids.

The active compounds of the present invention may be administered orally, parenterally, intravenously, rectally or by inhalation, the preferred administration being dependent on the specific clinical need of the disorder.

In this connection, the compounds of formula I can be used alone or together with pharmaceutical auxiliaries, and indeed both in veterinary and in human medicine.

Which auxiliaries are suitable for the desired pharmaceutical formulation is familiar to the person skilled in the art on the basis of his expert knowledge. In addition to solvents, gel-forming agents, suppository bases, tablet auxiliaries and other active compound carriers, antioxidants, dispersants, emulsifiers, defoaming agents, flavor correctors, preservatives, solubilizers or colorants, for example, can be used.

For a form for oral use, the active compounds are mixed with the additives suitable for this purpose, such as excipients, stabilizers or inert diluents and are brought into the forms suitable of administration, such as tablets, coated tablets, hard gelatin capsules, aqueous, alcoholic or oily solutions, by the customary methods. Inert carriers which can be used are, for example, gum arabic, magnesia, magnesium carbonate, potassium phosphate, lactose, glucose or starch, in particular cornstarch. In this case, preparation can take place both as dry and as moist granules. Suitable oily excipients or solvents are, for example, vegetable or animal oils, such as sunflower oil or cod liver oil.

For subcutaneous or intravenous administration, the active compounds, as desired with the substances customary for this purpose such as solubilizers, emulsifiers or other auxiliaries, are brought into solution, suspension or emulsion. Possible solvents are, for example: water, physiological saline solution or alcohols, for example ethanol, propanol, glycerol, in addition also sugar solutions such as glucose or mannitol solutions, or alternatively, a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of such solvents. If required, the formulation may also contain other pharmaceutical auxiliaries such as surfactants, emulsifiers and stabilizers and also a propellant gas. Such a preparation customarily contains the active compound in a concentration of about 0.1 to 10, in particular of about 0.3 to 3% by weight.

The dosage of the active compound of the formula I to be administered and the frequency of administration depend on the potency and duration of action of the compounds used; and additionally also on the nature and severity of the disease to be treated and on the sex, age, weight and individual responsiveness of the mammal to be treated.

On average, the daily dose of a compound of the formula I in a patient of about 75 kg weight is at least 0.001 mg, preferably 0.01 mg to at most 10 mg., preferably at most 1 mg. In acute outbreaks of the illness, for example immediately after suffering a cardiac infarct, still higher and above all, more frequent dosages may also be necessary, for example up to 4 individual doses per day. In particular on i.v. use, for example in an infarct patient in the intensive care unit, up to 100 mg per day may be necessary.

A few representative compounds of the formula I according to the invention or their physiologically tolerable salts shown below in Table I can be prepared analogously to the procedures given in the exemplary embodiments:

Table I 1) 2-(3,4-Dimethoxyphenyl)-4-guanidinocarbonyl-1(2H)-isoquinolinone. Hydrochloride monohydrate, m.p. 205°-206° C., 2) 2-(3-Methoxyphenyl)-4-guanidinocarbonyl-1(2H)-isoquinolinone. Hydrochloride, m.p. 238°-240° C., 3) 2-(4-Methoxyphenyl)-4-guanidinocarbonyl-1(2H)-isoquinolinone. Hydrochloride-hemihydrate, m.p. 249°-250° C., 4) 2-(3,5-Dimethoxyphenyl)-4-guanidinocarbonyl-1(2H)-isoquinolinone. Hydrochloride-sesquihydrate, m.p. 260°-262° C., 5) 2-(4-isopropylphenyl)-4-guanidinocarbonyl-1(2H)-isoquinolinone. Hydrochloride-Hydrate, m.p. 198°-200° C., 6) 2-(4-Chlorophenyl)-4-guanidinocarbonyl-1(2H)-isoquinolinone. Hydrochloride-Hydrate, m.p. 195°-197° C., 7) 2-(3,4-Dimethylphenyl)-4-guanidinocarbonyl-1(2H)-isoquinolinone. Hydrochloride-Hemihydrate, m.p. 248°-249° C., 8) 2-(4-Flurophenyl)-4-guanidinocarbonyl-1(2H)-isoquinolinone. Hydrochloride-Hemihydrate, m.p. 247°-248° C., 9) 2-(4-Ethoxyphenyl)-4-guanidinocarbonyl-1(2H)-isoquinolinone. Hydrochloride-Hemihydrate, m.p. 205°-207° C., 10) 2-(4-Cyclohexylphenyl)-4-guanidinocarbonyl-1(2H)-isoquinolinone. Hydrochloride, m.p. 253°-254° C., 11) 2-(2,4-Dimethylphenyl)-4-guanidinocarbonyl-1(2H)-isoquinolinone. Hydrochloride-Dihydrate, m.p. 218°-220° C., 12) 2-(2,5-Dimethylphenyl)-4-guanidinocarbonyl-1(2H)-isoquinolinone. Hydrochloride-hydrate, m.p. 210°-211° C., 13) 2-(4-Methylphenyl)-4-guanidinocarbonyl-1(2H)-isoquinolinone. Hydrochloride-Hemihydrate, m.p. 245°-246° C., 14) 2-(2-Methylphenyl)-4-guanidinocarbonyl-1(2H)-isoquinolinone. Hydrochloride, m.p. 274°-275° C., 15) 2-(3,5-Dimethylphenyl)-4-guanidinocarbonylol-1(2H)-isoquinolinone. Hydrochloride, m.p. 281°-282° C., 16) 2-(3-Methylphenyl)-4-guanidinocarbonyl-1(2H)-isoquinolinone. Hydrochloride, m.p. 269°-270° C., 17) 2-(2-Naphthyl)-4-guanidinocarbonyl-1(2H)-isoquinolinone. Hydrochloride, m.p. 217°-219° C., 18) 6,7-Dimethoxy-2-(3,4-dimethylphenyl)-4-guanidinocarbonyl-1(2H)-isoquinolinone. Hydrochloride, m.p. 270°-271° C., 19) 6,7-Dimethoxy-2-(3-methoxyphenyl)-4-guanidinocarbonyl-1(2H)-isoquinolinone. Hydrochloride, m.p. 259°-263° C., 20) 2-(3,4-Dimethylphenyl)-4-guanidinocarbonyl-6-methyl-1(2H)-isoquinolinone hydrochloride hemihydrate. m.p. 305°-306° C.

21) 4-Guanidinocarbonyl-6-methyl-2-(2-methylphenyl)-1(2H)-isoquinolinone hydrochloride. m.p. 303°-305° C.

22) 4-Guanidinocarbonyl-6-methyl-2-(4-methoxyphenyl)-1(2H)-isoquinolinone hydrochloride hemihydrate. m.p. 251°-253° C.

23) 2-(3,5-Dimethoxyphenyl)-4-guanidinocarbonyl-6-methyl-1(2H)-isoquinolinone hydrochloride sesquihydrate. m.p. 261°-263° C.

24) 4-Guanidinocarbonyl-2-(3-methoxyphenyl)-6-methyl-1(2H)-isoquinolinone hydrochloride hemihydrate. m.p. 262°-264° C.

25) 4-Guanidinocarbonyl-6-methyl-2-(3-methylphenyl)-(2H)-isoquinolinone hydrochloride. m.p. 288°-290° C.

26) 4-Guanidinocarbonyl-6-methyl-2-phenyl-1(2H)-isoquinolinone hydrochloride. m.p. 282°-283° C.

27) 2-(4-Chlorophenyl)-4-guanidinocarbonyl-6-methyl-1(2H)-isoquinolinone hydrochloride monohydrate. m.p. 273°-275° C.

28) 4-Guanidinocarbonyl-6-methyl-2-(2-naphthyl)-1(2H)-isoquinolinone hydrochloride. m.p. 270°-271° C.

29) 2-(2,4-Dimethylphenyl)-4-guanidinocarbonyl-6-methyl-1(2H)-isoquinolinone hydrochloride. m.p. 219°-220° C.

30) 4-Guanidinocarbonyl-6-methyl-2-(2,4,6-trimethylphenyl)-1(2H)-isoquinolinone hydrochloride sesquihydrate. m.p. 261°-262° C.

31) 4-Guanidinocarbonyl-2-(2-methoxyphenyl)-6-methyl-1(2H)-isoquinolinone hydrochloride hemihydrate. m.p. 284°-285°C.

32) 2-(2,6-Dimethylphenyl)-4-guanidinocarbonyl-6-methyl-1(2H)-isoquinolinone hydrochloride hemihydrate. m.p. 283° C.

33) 4-Guanidinocarbonyl-6-methyl-2-(3,4,5-trimethoxyphenyl)-1(2H)-isoquinolinone hydrochloride dihydrate. m.p. 250° C.

34) 2-(4-Bromophenyl)-4-quanidinocarbonyl-6-methyl-1(2H)-isoquinolinone hydrochloride hemihydrate. m.p. 259-260.

35) 2-84-Fluorophenyl)-4-guanidinocarbonyl-6-methyl-1(2H)-isoquinolinone hydrochloride. m.p. 260°–261° C.
36) 2-(4-Fluorophenylmethyl)-4-guanidinocarbonyl-6-methyl-1(2H)-isoquinolinone hydrochloride. m.p. 251°–252° C.
37) 4-Guanidinocarbonyl-6-methyl-2-phenylmethyl-1(2H)-isoquinolinone hydrochloride. m.p. 257°–258° C.
38) 2-(4-Chlorophenylmethyl)-4-guanidinocarbonyl-6-methyl-1(2H)-isoquinolinone hydrochloride hemihydrate. m.p. 265° C.
39) 2-(2-Fluorophenyl)-4-guanidinocarbonyl-6-methyl-1(2H)-isoquinolinone hydrochloride monohydrate. m.p. 275° C.
40) 4-Guanidinocarbonyl-6-methyl-2-(4-nitrophenyl)-1(2H)-isoquinolinone hydrochloride monohydrate. m.p. 262°–263° C.
41) 2-(3,4-Dimethoxyphenylmethyl)-4-guanidinocarbonyl-6-methyl-1(2H)-isoquinolinone hydrochloride hemihydrate. m.p. 228°–230° C.
42) 2-Cyclopentyl-4-guanidinocarbonyl-6-methyl-1(2H)-isoquinolinone hydrochloride. m.p. 253°–254° C.
43) 4-Guanidinocarbonyl-6-methyl-2-(1-methylethyl)-1(2H)-isoquinolinone hydrochloride. m.p. 258°–259° C.
44) 2-(4-Bromo-2,6-dimethylphenyl)-4-guanidinocarbonyl-6-methyl-1(2H)-isoquinolinone hydrochloride. m.p. 251°–252° C.
45) 2-(3,4-Dichlorophenylmethyl)-4-guanidinocarbonyl-6-methyl-1-(2H)-isoquinolinone hydrochloride. m.p. 251°–252° C.
46) 4-Guanidinocarbonyl-6-methyl-2-[4-(1-piperazinophenyl)]-1(2H)-isoquinolinone dihydrochloride dihydrate. m.p. >360° C.
47) 2-(3-Fluorophenyl)-4-guanidinocarbonyl-6-methyl-1(2H)-isoquinolinone hydrochloride. m.p. 278°–280° C.
48) 2-Phenyl-4-guanidinocarbonyl-1(2H)-isoquinolinone hydrochloride hemihydrate. m.p. 251°–255° C.
49) 2-(3,4,5-Trimethoxyphenyl)-4-guanidinocarbonyl-1(2H)-isoquinolinone hydrochloride dihydrate. m.p. 264°–269° C.
50) 2-(2-Chloro-4-methyl)-4-guanidinocarbonyl-1(2H)-isoquinolinone hydrochloride hemihydrate. m.p. 220°–225° C.
51) 2-(2,4-Dimethoxyphenyl)-4-guanidinocarbonyl-1(2H)-isoquinolinone hydrochloride sesquihydrate. m.p. 216° C.
52) 6,7-Dimethoxy-2-(2-naphthyl)-4-guanidinocarbonyl-1(2H)-isoquinolinone hydrochloride sesquihydrate. m.p. 277°–280° C.
53) 6,7-Dimethoxy-2-(3-methoxyphenyl)-4-guanidinocarbonyl-1 (2H)-isoquinolinone hydrochloride hydrate. m.p. 259°–263° C.
54) 2-(4-t-Butylphenyl)-4-guanidinocarbonyl-1(2H)-isoquinolinone hydrochloride hydrate m.p. 230°–235° C.
55) 2-Ethyl-4-guanidinocarbonyl-1(2H)-isoquinolinone hydrochloride hydrate. m.p. 264°–269° C.
56) 2-(2-Ethoxyphenyl)-4-guanidinocarbonyl-1(2H)-isoquinolinone hydrochloride hydrate. m.p. 204°–206° C.
57) 2-1Isopropyl-4-guanidinocarbonyl-1(2H)-isoquinolinone hydrochloride. m.p. m.p. 248°–273° C.
58) 2-Cyclopentyl-4-guanidinocarbonyl-1(2H)-isoquinolinone hydrochloride. m.p. 244°–249° C.
59) 2-Propyl-4-guanidinocarbonyl-1(2H)-isoquinolinone hydrochloride. m.p. 248°–254° C.
60) 2-(4-N,N-Dimethylphenyl)-4-guanidinocarbonyl-1(2H)-isoquinolinone hydrochloride hydrate. m.p. 225°–227° C.
61) 2-iso-Butyl-4-guanidinocarbonyl-1(2H)-isoquinolinone hydrochloride hydrate. m.p. 242°–244° C.
62) 2-(2-Methyl-6-pyridyl)-4-guanidinocarbonyl-1(2H)-isoquinolinone dihydrochloride hemihydrate. m.p. 219°–221° C.
63) 2-(2,3-Dihydro-1,5-dimethyl-2-phenyl-3-oxo-4-pyrazolyl)-
64) 2-(2-Methoxy-4-methylphenyl)-4-guanidinocarbonyl-1(2H)-isoquinolinone hydrochloride dihydrate. m.p. 212°–213° C.
65) 2-(2-Methoxyphenyl)-4-guanidinocarbonyl-1(2H)-isoquinolinone hydrochloride. m.p. 268°–269° C.
66) 2-(3-Chlorophenyl)-4-guanidinocarbonyl-1(2H)-isoquinolinone hydrochloride hydrate. m.p. 269°–270° C.
67) 2-Cyclohexyl-4-guanidinocarbonyl-1(2H)-isoquinolinone hydrochloride sesquihydrate. m.p. 189°–190° C.
68) 4-Guanidinocarbonyl-2-(3-hydroxyphenyl)-1(2H)-isoquinolinone hydrochloride sesquihydrate. m.p. 219°–221° C.
69) 2-(5-Fluoro-2-methylphenyl)-4-guanidinocarbonyl-1(2H)-isoquinolinone hydrochloride hydrate. m.p. 214°–216° C.
70) 4-Guanidinocarbonyl-2-(1-naphthyl)-1(2H)-isoquinolinone hydrochloride sesquihydrate. m.p. 231°–232° C.
71) 2-[2-(3,4-Dimethoxyphenylethyl)]-4-guanidinocarbonyl-1(2H)-isoquinolinone hydrochloride hemihydrate. m.p. 282°–283° C.
72) 2-(2,4-Dichlorophenyl)-4-guanidinocarbonyl-1(2H)-isoquinolinone hydrochloride hydrate. m.p. 254°–255° C.
73) 4-Guanidinocarbonyl-2-(2,4,6-trimethylphenyl)-1(2H)-isoquinolinone hydrochloride hemihydrate. m.p. 280°–282° C.
74) 4-Guanidinocarbonyl-2-(5-methylisoxazol-3-yl)1(2H)-isoquinolinone hydrochloride hemihydrate. m.p. 253°–255° C.
75) 2-(2,6-Difluorophenyl)-4-guanidinocarbonyl-1(2H)-isoquinolinone hydrochloride. m.p. 261°–262° C.
76) 2-(3,4-Dichlorobenzyl)-4-guanidinocarbonyl-1(2H)-isoquinolinone hydrochloride. m.p. 255°–257° C.
77) 2-(4-Fluorobenzyl)-4-guanidinocarbonyl-1(2H)-isoquinolinone hydrochloride. m.p. 263°–264° C.
78) 2-(4-Chlorobenzyl)-4-guanidinocarbonyl-1(2H)-isoquinolinone hydrochloride hydrate. m.p. 249°–250° C.

Experimental Section

The representative example 2-(2-Methylphenyl)-4-guanidino-carbonyl-1(2H)-isoquinolinone (S. No. 14 of formula I—Table I) is defined: other compounds were also synthesized using such/other sequences.

A. Synthesis of compound with formula II.

a: 4-(2-Methylphenyl) aminomethylene homophthalic anhydride:

Homophthalic anhydride (2.4 g), triethylorthoformate (11 ml) and o-toluidine (1.6 g) were mixed and refluxed for 40 min. The reaction mixture was cooled, diluted with ethanol and petroleum ether to give a solid. The solid was filtered washed with pet ether; yield 2.05 g; mp 289°–290° C., IR (KBr)in cm$^{-1}$, 1700, 1665 and 1510. Anal calcd. for: $C_{17}H_{13}NO_3$; C, 73.11%; H, 4.69; N, 5.01%. Found: C, 72.58% H,4.75%; N, 4.93%.

B. Synthesis of compounds with formula III.

a. 2-(2-Methylphenyl)-4-carboxy-1(2H) isoquinolinone:

4-(2-Methylphenyl)aminomethylene homophthalic anhydride (1.85 g), ethyl alcohol (25 ml) and sodium hydroxide (1.3 g) were mixed and heated on a steam bath for 1hour. The reaction mixture was diluted with water and acidified with diluted hydrochloric acid. The separated solid was filtered and washed with water and dried. Traces of impurities by flash chromatography using 1% MeOH-CHCl$_3$ as the eluant.

Yield 844 mg; mp 307°-308° C.

IR(KBr)in cm$^{-1}$, 3040-3100 (broad); 1720,1655, NMR(CDCl$_3$+TFA) δ: 2.2. (S, 3H, Ar—CH$_3$); 7.2-7.4 (m, 4H, Ar—H); 7.6-8.0 (m, 2H, Ar—H); 8.32 (S, IH, H-3); 8.48 (d,J=7.7Hz, IH, H-5); 8.88(d,J=7.7Hz, IH, H-8).

|  | C % | H % | N % |
|---|---|---|---|
| Anal Calcd. for $C_{17}H_{13}NO_3$: | 73.11 | 4.69 | 5.01 |
| Found: | 72.69 | 4.78 | 4.99 |

C. Synthesis of compounds with formula I.

a. 2-(2-Methylphenyl)-4-guanidinocarbonyl-1(2H)-isoquinolinone.

2-(2-Methylphenyl)-4-carboxy-1(2H)-isoquinolinone (0.78 g) was dissolved in dry DMF (12 ml), 1,1-Carbonyldiimidazole (500 mg) was added and the reaction mixture stirred at room temperature for 3 hrs., the resultant solution was transferred to a flask containing free guanidine (0.95 g). The reaction mixture was further stirred at room temperature for overnight. Excess solvent was removed under vacuum. The residue was triturated with water and the separated solid was filtered, washed with water and dried. Yield 787 mg;

The compound was converted into hydrochloride salt, Yield 746 mg; mp 274°-275° C.

IR(KBr) in cm$^{-1}$; 3350-2900; 1700; 1670 and 1620. NMR (DMSO-d$_6$) in δ: 2.2 (S, 3H, Ar—CH$_3$); 7.44 (brS, 4H, Ar—H); 7.56-7.96 (m, 2H, Ar—H); 8.04-8.60 [m, 7H, Ar—H(3); NH$_2$(4)], 12.23 (brS, IH, H-Cl).

|  | C % | H % | N % | Cl % |
|---|---|---|---|---|
| Anal. Calc. for: $C_{18}H_{17}N_4O_2Cl$: | 60.59 | 4.80 | 15.70 | 9.93 |
| Found: | 60.55 | 4.75 | 15.51 | 10.05. |

Pharmacological methods to evaluate antiarrhythmic and cardioprotective action:

1. Reperfusion induced arrhythmias in isolated rat heart.

Wistar rats of either sex, weighing 280-300 g were used in this experiment. The heart was excised and perfused with physiological solution according to Langendorff method. The perfusate was gassed with 95% oxygen and 5% carbon dioxide gas mixture at 37° C. A silicon balloon catheter was introduced the left ventricle through the left auricle for recording left ventricular pressure (LVP) and left ventricular dP/dt max. (LV dp/dE max). The heart was perfused for an initial 20 min period (control perfusion). Acute regional ischemia was then induced in the left anterior descending coronary artery for 15 rain (ischemic period). Thereafter, the occlusion was reopened and cardiac functions were monitored for 30 min. (reperfusion period).

The following parameters such as LVP, LV dp/dt max, heart rate, coronary flow, ventricular fibrillation (VF) duration were recorded continuously on Nihon-Kohden polygraph system. Epicordial ECG was monitored on BPL monitor throughout the experiment.

All test compounds were dissolved in distilled water or DMSO (100%) and added in different concentrations into perfusate. The protective effect of the compound was assessed from reduction in VF duration and reversal of cardiac contractility. The results of the representative compounds are cited in the table II. The instant compounds of the series, at 0.1 μM-1.0 μM dose, as compared to control heart, significantly reduced the duration of reperfusion induced arrhythmias (Ref. Table II).

TABLE II

Reperfusion induced arrhythmias in isolated rat heart.

| *S.No. | n | Dose μM | Ventricular Fibrillation Duration (Min) M ± S.E. |
|---|---|---|---|
| Control | 8 | — | 26.25 ± 3.75 |
| 2 | 7 | 1 | 3.14 ± 2.65 |
| 4 | 6 | 1 | 10.11 ± 6.29 |
| 7 | 7 | 0.1 | 4.32 ± 4.28 |
| 13 | 7 | 0.1 | 12.86 ± 6.03 |
| 14 | 4 | 0.1 | 7.5 ± 7.5 |

*S.No.: Refers to numbers in the Table I.

We claim:

1. An isoquinoline compound of the formula I:

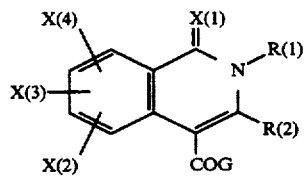

wherein:

R(1) is hydrogen, (C$_1$-C$_6$)-alkyl, (C$_3$-C$_8$)-cycloalkyl, phenyl- (C$_1$-C$_6$)-alkyl, (C$_3$-C$_6$)-alkenyl, substituted (C$_1$-C$_6$)-alkyl-amino or a phenyl, naphthyl, pyridyl, thienyl, furyl, indolyl, quinolyl, isoquinolyl, pyrimidyl, triazolyl, benzothiazolyl, pyrrolidinyl, piperidinyl, morpholinyl, or piperazinyl ring, the rings being unsubstituted or substituted with one to three substituents selected from the group consisting of F, Cl, Br, I, nitro, amino, mono-(C$_1$-C$_6$)-alkyl-amino, di-(C$_1$-C$_6$)-alkyl-amino, (C$_1$-C$_6$)-alkyl, (C$_1$-C$_6$)-alkoxy, benzyloxy, phenoxy, hydroxy, and trifluoromethyl;

R(2) is hydrogen, F, Cl, Br, I, (C$_1$-C$_6$)-alkyl, or phenyl which is unsubstituted or is substituted by one to three substituents selected from the group consisting of F, Cl, Br, I, nitro, amino, mono-(C$_1$-C$_6$)-alkyl-amino, di-(C$_1$-C$_6$)-alkyl-amino, (C$_1$-C$_6$)-alkyl, (C$_1$-C$_6$)-alkoxy, benzyloxy, phenoxy and hydroxy;

G is a radical of the formula VII:

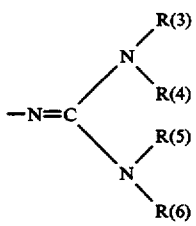

X(2), X(3) and X(4) are individually or collectively hydrogen, F, Cl, Br, I, nitro, amino, alkyl, sulfonamide, mono-($C_1$-$C_6$)-alkyl-amino, di-($C_1$-$C_6$)-alkyl-amino, ($C_1$-$C_6$)-alkyl, benzyloxy, or hydroxy; and X(1) is hydrogen, oxygen, sulfur or NR(7), in which R(7) is hydrogen, ($C_1$-$C_6$)-alkyl, ($C_3$-$C_6$)-cycloalkyl, phenyl-($C_1$-$C_6$)-alkyl, ($C_3$-$C_6$)-alkenyl, substituted ($C_1$-$C_6$)-or a phenyl, pyridyl, thienyl, furyl, indolyl, quinolyl, isoquinolyl, pyrimidyl, triazolyl, benzothiazolyl, pyrrolidinyl, piperidinyl, morpholinyl, or piperazinyl ring, which rings are unsubstituted or substituted with one to three substituents selected from the group consisting of F, Cl, Br, I, nitro, amino, mono-($C_1$-$C_6$)-alkyl-amino, di-($C_1$-$C_6$)-alkyl-amino, ($C_1$-$C_6$)-alkyl, ($C_1$-$C_6$)-alkoxy, benzyloxy, phenoxy, hydroxy, and trifluoromethyl, in which substituents any alkyl chain or alkenyl chain may be interrupted by oxygen, sulfur or NR(8) wherein R(8) is hydrogen, ($C_1$-$C_6$)-alkyl, ($C_3$-$C_8$)-cycloalkyl, phenyl-($C_1$-$C_6$)-alkyl, ($C_3$-$C_6$)-alkenyl, substituted ($C_1$-$C_6$)-alkyl-amino or a phenyl, pyridyl, thienyl, furyl, indolyl, quinolyl, isoquinolyl, pyrimidyl, triazolyl, benzothiazolyl, pyrrolidinyl, piperidinyl, morpholinyl or piperazinyl ring, which rings are unsubstituted or substituted with one to three substituents selected from the group consisting of F, Cl, Br, I, nitro, amino, mono-($C_1$-$C_6$)-alkyl-amino, di-($C_1$-$C_6$)-alkyl-amino, ($C_1$-$C_6$)-alkyl, ($C_1$-$C_6$)-alkoxy, benzyloxy, phenoxy, hydroxy and trifluoromethyl, or a pharmaceutically acceptable salt thereof.

2. A compound of the formula I as claimed in claim 1 in which:

R(1) is phenyl, naphthyl, pyridyl, thienyl, furyl, indolyl, quinolyl, isoquinolyl, pyrimidyl, triazolyl, benzothiazolyl, pyrrolidinyl, piperidinyl, morpholinyl, or piperazinyl, unsubstituted or substituted with one to three substituents selected from the group consisting of F, Cl, Br, I, nitro, amino, mono-($C_1$-$C_6$)-alkyl-amino, di-($C_1$-$C_6$)-alkyl-amino, ($C_1$-$C_6$)-alkyl, ($C_1$-$C_6$)-alkoxy, benzyloxy, phenoxy, hydroxy and trifluoromethyl;

R(2) is hydrogen, or ($C_1$-$C_6$)-alkyl;

G is a radical of the formula VII:

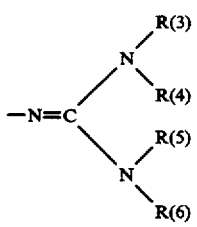

R(3), R(4), R(5) and R(6) are hydrogen;

X(2), X(3) and X(4) are individually or collectively hydrogen, F, Cl, Br, I, nitro, amino, ($C_1$-$C_6$)-alkyl, sulfonamide, mono-($C_1$-$C_6$)-alkyl-amino, di-($C_1$-$C_6$)-alkyl-amino, ($C_1$-$C_6$)-alkyl, benzyloxy or hydroxy; and X(1) is oxygen.

3. A compound of the formula I as claimed in claim 1 wherein:

R(1) is($C_1$-$C_6$)-alkyl, ($C_1$-$C_6$)-alkyloxy, or a phenyl, naphthyl, or pyridyl ring, the rings being unsubstituted or substituted with one to three substituents selected from the group consisting of F, Cl, Br, I, nitro, amino, mono-($C_1$-$C_6$)-alkyl-amino, di-($C_1$-$C_6$)-alkyl-amino, ($C_1$-$C_6$)-alkyl, ($C_1$-$C_6$)-alkoxy benzyloxy, phenoxy, hydroxy and trifluoromethyl;

R(2) is hydrogen;

G is a radical of the formula VII:

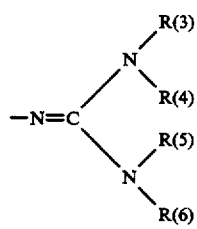

with R(3), R(4), R(5) and R(6) being hydrogen;

X(2), X(3) and X(4) are individually or collectively hydrogen, F, Cl, Br, I, nitro, amino, alkyl, sulfonamide, mono-($C_1$-$C_6$)-alkyl-amino, di-($C_1$-$C_6$)-alkyl-amino, ($C_1$-$C_6$)-alkyl, benzyloxy or hydroxy; and X(1) is oxygen.

4. A compound of the formula I as claimed in claim 1 wherein:

R(1) is ($C_1$-$C_6$)-alkyl, ($C_1$-$C_6$)-alkyloxy, or a phenyl, naphthyl or pyridyl ring, the rings being unsubstituted or substituted with Cl;

R(2) is hydrogen;

G is a radical of the formula VII:

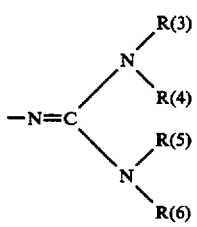

with R(3), R(4), R(5) and R(6) being hydrogen;

X(2), X(3) and X(4) are individually or collectively hydrogen, F, Cl, Br, I, nitro, amino, ($C_1$-$C_6$)-alkyl, sulfonamide, mono-($C_1$-$C_6$)-alkyl-amino, di-($C_1$-$C_6$)-alkyl-amino, ($C_1$-$C_6$)-alkyl, benzyloxy or hydroxy; and X(1) is oxygen.

5. A medicament pharmaceutical composition for combating or preventing heart failure or ischemic conditions of the heart which comprises an effective amount of a compound of the formula I as claimed in claim 1 together with a pharmaceutically acceptable auxiliary.

6. A method of treating or preventing heart failures which comprises administering an effective amount of a compound of the formula I as claimed in claim 1.

7. A method of treating or preventing ischemic conditions of the heart which comprises administering an effective amount of a compound of the formula I as claimed in claim 1.

* * * * *

UNITED STATES PATENT AND TRADEMARK OFFICE
CERTIFICATE OF CORRECTION

PATENT NO. : 5,416,094
DATED : May 16, 1995
INVENTOR(S) : Bansi LAL et al

It is certified that error appears in the above-indentified patent and that said Letters Patent is hereby corrected as shown below:

Claim 1, Column 13, Line 17, change "$(C_3-C_6)$" to --$(C_3-C_8)$--.

Claim 1, Column 13, Line 19, after "$(C_1-C_6)$" insert --alkyl-amino--.

Claim 5, Column 14, Line 56, before "pharmaceutical composition" delete "medicament".

Signed and Sealed this

Seventh Day of November, 1995

Attest:

BRUCE LEHMAN

*Attesting Officer*  *Commissioner of Patents and Trademarks*